July 6, 1937. E. A. BRIGGS Plant Pat. 255
GLADIOLUS
Filed Nov. 2, 1936
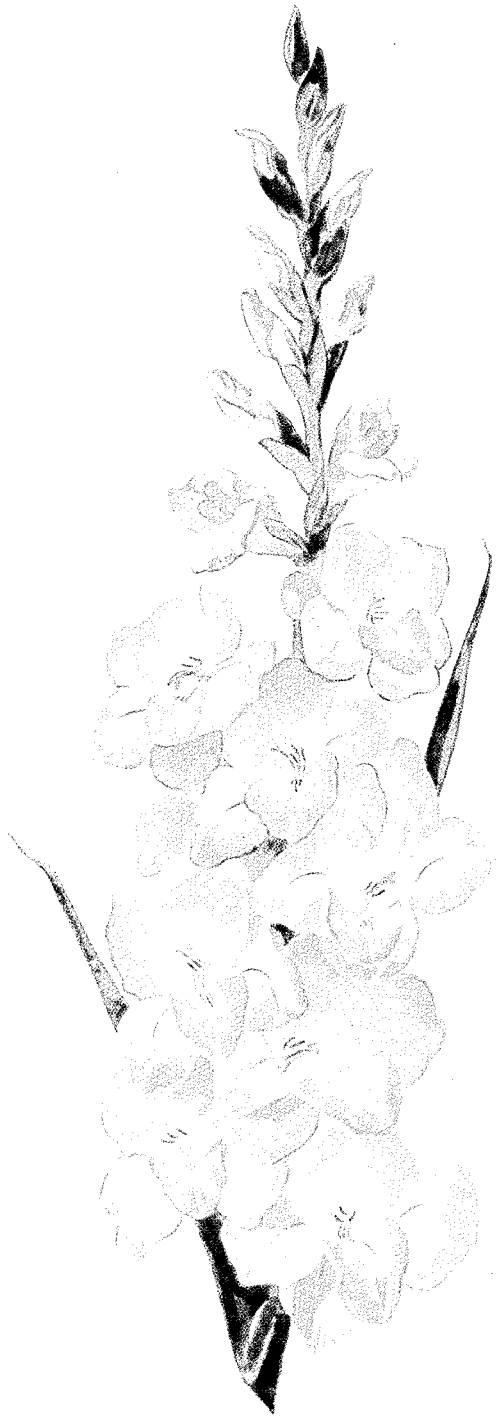
INVENTOR
Elizabeth A. Briggs Patented July 6, 1937

Plant Pat. 255

UNITED STATES PATENT OFFICE

255

GLADIOLUS

Elizabeth A. Briggs, Encinitas, Calif.

Application November 2, 1936, Serial No. 108,837

1 Claim. (Cl. 47—60)

My present invention relates to improvements in gladioli of the lavender or phlox pink color and of the type notable for size and quantity and lasting qualities of bloom. The object of this invention is to provide a gladiolus of superior lavender or phlox pink coloring combined with exceptionally tall spikes of flowers bearing a large number of large-sized and exceptionally well-shaped flowers, as well as possessing superior keeping qualities when cut.

My new variety of gladiolus originated as a seedling produced from cross pollination work carried on by myself. To the best of my knowledge and belief the parents of this new variety were the variety "W. H. Phipps" and an unnamed phlox pink variety produced by myself. It first bloomed in June 1931. "W. H. Phipps" was the result of a cross (parents unknown to this applicant) made by Richard Diener at Kentfield, California. The unnamed phlox pink seedling was the result of a hand pollinated cross by the applicant between "Minuet", the pollen parent, and "Berty Snow", the seed bearing parent. "Berty Snow" was originated by Mair & Sons of Scotland. "Minuet" was originated by Joe Coleman of Sanford, Florida. The breeding of these two varieties is not known to this applicant. This applicant takes no precaution to prevent admixture of pollen by wind or insects in making her crosses.

The accompanying illustration shows as nearly as the artist could paint it, a flowering spike as it would normally appear when fresh cut, also some of the foliage. The painting does not, however, convey the full beauty of the flowers as viewed in nature where the great size is appreciated and each flower stands out clearly yet displays a softness of coloring impossible to depict with paints on paper.

The plant is a vigorous grower and the tips of the spikes usually reach a height of 50 inches above the ground. Foliage is heavy in quantity and dark green in color.

Reproduction is very rapid because of the large number of cormels or cormlets produced.

The spikes are taller than those of somewhat similar lavender or phlox pink varieties grown under same conditions of soil and climate. The spikes ordinarily have 18 buds and 6 to 8 of these will be opened at one time. Lavender and phlox pink varieties somewhat similar to this new variety, such as "Berty Snow" and "Minuet" fall far short of the size of flower, length of spike, vigor in starting growing from bulblets, keeping qualities and smoothness of color of this new variety; "Minuet" being shorter in height, having fewer blooms open and being poorer in starting growth from bulblets, and "Berty Snow" being smaller in flower, having poorer keeping qualities and lacking the same smoothness in color.

The flowers are each considerably larger than those of either "Berty Snow" or "Minuet" in addition to occurring more to the spike. A typical flower at the bottom of the spike will measure 6 inches across.

The color most nearly approaches "phlox pink", according to Ridgway's Color Standards and Nomenclature, edition of 1912, Plate XI. In addition it has a light feather in the throat on the two lower petals of "phlox purple", according to Ridgway's Color Standards, edition of 1912, Plate XI. The color is more pleasing and smoother than shown by either "Minuet" or "Berty Snow", varieties above mentioned.

Another notable characteristic of this new variety that makes it particularly valuable to the florist, is that all the buds bloom out well when the spike is cut and placed in water. Even the topmost bud will develop fully under these circumstances. This is a characteristic not equally possessed by either of the varieties "Minuet" or "Berty Snow".

The substance of the flowers is substantial and gives them excellent keeping and shipping qualities.

The most notable characteristics which readily distinguish my new variety of gladiolus from all other lavender or phlox pink varieties and particularly from the varieties known as "Minuet" and "Berty Snow" are:

First, the beauty and smoothness of color of the blooms.

Second, the height, vigor and productivity of the plant.

Third, the exceptional keeping qualities of the flower.

Fourth, the large size of bloom.

Having thus disclosed my invention, I claim:

The variety of gladiolus plant herein described and illustrated, characterized particularly by the unusual beauty and smoothness of color, together with the unusual height, vigor and productivity, combined with exceptional keeping qualities and size of bloom.

ELIZABETH A. BRIGGS.